(12) United States Patent
Choi

(10) Patent No.: US 6,875,195 B2
(45) Date of Patent: Apr. 5, 2005

(54) PORTABLE AUTOMATIC INSULIN SYRINGE DEVICE WITH BLOOD SUGAR MEASURING FUNCTION

(76) Inventor: Soo Bong Choi, #5-908, Youwon Apt., 421-7 Yeonsoo-dong, Chungju-shi, Chungcheongbuk-do (KR)

( * ) Notice: Subject to any disclaimer, the term of this patent is extended or adjusted under 35 U.S.C. 154(b) by 29 days.

(21) Appl. No.: 09/960,463

(22) Filed: Sep. 19, 2001

(65) Prior Publication Data

US 2003/0055323 A1 Mar. 20, 2003

(51) Int. Cl.$^7$ ............................................. A61M 31/00

(52) U.S. Cl. ........................................ 604/66; 604/504

(58) Field of Search ................................. 600/347, 365; 422/50, 55, 58, 82.05, 68.1; 604/187, 65, 67, 504, 891.1, 66; 435/4, 14

(56) References Cited

U.S. PATENT DOCUMENTS

| | | | |
|---|---|---|---|
| 4,417,889 A | | 11/1983 | Choi |
| 5,281,395 A | * | 1/1994 | Markart et al. .......... 422/82.05 |
| 5,316,727 A | * | 5/1994 | Suzuki et al. ............... 422/68.1 |
| 6,192,891 B1 | * | 2/2001 | Gravel et al. ............... 604/187 |
| 2002/0193679 A1 | * | 12/2002 | Malave et al. ................ 604/65 |

* cited by examiner

*Primary Examiner*—Eric F. Winakur
(74) *Attorney, Agent, or Firm*—Sheridan Ross PC

(57) ABSTRACT

Disclosed is a portable automatic insulin syringe device adapted to enable an injection of liquid medicine for a prolonged time, including a syringe pump having a pump housing, further including a blood sugar measuring unit mounted at one side of the pump housing and adapted to measure a blood sugar level of a user, a control unit for controlling the blood sugar measuring unit and the syringe pump, and a display unit for simultaneously displaying the quantity of insulin dispensed to a user and the blood sugar level measured by the blood sugar measuring unit.

1 Claim, 22 Drawing Sheets

PORTABLE AUTOMATIC INSULIN SYRINGE DEVICE WITH BLOOD SUGAR MEASURING FUNCTION

BACKGROUND OF THE INVENTION

1. Field of the Invention

The present invention relates to a portable automatic insulin syringe device capable of measuring and displaying the quantity of insulin dispensed to the user and the blood sugar level of the user, while having an automatic insulin injecting function. In particular, the present invention provides a portable automatic insulin syringe device which is adapted to automatically dispense insulin to the user for a prolonged time, and includes a blood sugar measuring unit mounted in a syringe device housing and adapted to measure the blood sugar level of the user, and a control unit adapted to receive a measured value from the blood sugar measuring unit, thereby performing a control for displaying the measured value along with the quantity of insulin dispensed to the user, so that the syringe device can measure the blood sugar level of the user.

2. Description of the Related Art

Diabetes is known to affect more than one hundred million individuals worldwide at the present time, assuming there are about six billion people worldwide. For instance, in Korea, it is believed that diabetes affects about two million individuals. It is also estimated that 10% of patients with internal diseases suffer from diabetes in Korea. There is no cure for diabetes although it can be controlled. If a diabetic patient fails to control his disease, he may develop complications, thereby endangering his life. For instance, in Korea, the death rate due to diabetes is increasing gradually. In 1990, 11.5 individuals per one hundred thousand population died of the disease. Thus, diabetes is known as a fatal disease.

Diabetes is a disease symptomized by an increase in blood sugar levels exceeding 140 mg/dl on an empty stomach, or 200 mg/dl 2 hours after a meal. The cause of such increased in blood sugar levels is not yet clearly known. An abnormality in the production of insulin, serving to promote assimilation of sugar, is the only cause known heretofore. Such an abnormality may be an insulin deficiency, caused by an insufficient quantity of insulin secreted by the β-cells of the pancreas. Otherwise, an increase in blood sugar level is caused by a degradation in the function of insulin, occurring for unknown reasons, thereby resulting in an insufficient assimilation of blood sugar, even though a desired quantity of insulin is normally secreted by the β-cells of the pancreas. Such a degradation in the function of insulin is called "insulin resistance". Diabetes resulting from an absolute insulin deficiency is called an "insulin-dependent diabetes" whereas diabetes resulting from an insufficient function of insulin in spite of a sufficient secretion of insulin is called a "noninsulin-dependent diabetes". Recently, the possibility of an intermediate type between the insulin-dependent diabetes and non-insulin-dependent diabetes has also been discussed. It is difficult to accurately determine whether a diabetic patient is insulin-dependent or non-insulin-dependent. Known methods for treatment of diabetes are classified into dietary treatment, exercise treatment, medicinal therapy, and insulin injections. A pancreas transplant is also a possible option.

Although insulin injection is a treatment used for patients with insulin-dependent diabetes, it may also be effective for patients with non-insulin-dependent diabetes. In accordance with the insulin injection method, it is normal that insulin is dispensed to a diabetic patient one or two times daily by injection. The quantity of insulin secreted in the human body is irregular in that an increased quantity of insulin is secreted three times daily, before and after respective mealtimes, while a reduced quantity of insulin is secreted at other times. For this reason, insulin is dispensed at a steady rate in accordance with the above mentioned insulin injection. This results in a high blood sugar level for a certain period of time after every mealtime because of an insulin deficiency, while resulting in a low blood sugar level at night because of an excessive secretion of insulin. That is, the above mentioned insulin injection method involves an abnormal dispensation of insulin, thereby causing an abnormality of the body. The reason why conventional insulin injection methods cannot contribute to the prevention of any complications from diabetes is because they cannot control the dispensation of insulin in accordance with a variation in the quantity of endogenous insulin naturally secreted in the body of a healthy person. To this end, improved treatment methods have been proposed. One method is to use an insulin pump (namely, a mechanical artificial pancreas) adapted to control the quantity of dispensed insulin using a computer in such a fashion that the dispensation of insulin approximates the secretion of insulin in the body of a healthy person. Another method is a surgical operation method for transplanting the β-cells of the pancreas. In accordance with this pancreas transplant method, the β-cells of the pancreas of a healthy person are transplanted to a diabetic patient so that the diabetic patient normally secretes insulin to normally control his blood sugar level. However, the pancreas transplant method involves immunological rejection complications and other associated problems. This pancreas transplant method was studied in U.S.A. from 1974 and practiced by Professor Temberane at Yale University in U.S.A. from 1979.

Automatic syringe devices, which enable an injection of liquid medicine for a prolonged time, are well known. Such automatic syringe devices are called "insulin pumps", "insulin syringe devices", or "automatic insulin syringe devices". Typically, known automatic syringe devices have a configuration in which a pushing means for pushing a syringe piston is coupled to a housing receiving an injection syringe. For example, such automatic syringe devices are disclosed in Japanese Utility Model Laid-open Publication No. Sho. 52-3292 and U.S. Pat. No. 4,417,889. The syringe device disclosed in Japanese Utility Model Laid-open Publication No. Sho. 52-3292 has inconvenience in its carriage because it has an injector mounted outside a basic case, thereby requiring a double case structure. In order to solve such a disadvantage, an automatic syringe device requiring no double case structure has been proposed, as in the above mentioned U.S. Pat. No. 4,417,889. FIGS. 1 and 2 illustrate a control circuit and a structure of the automatic syringe device disclosed in U.S. Pat. No. 4,417,889, respectively. Referring to FIG. 1, the output of an oscillator A1 is coupled to a timer A2 which is, in turn, coupled at its output to a digital comparator A3. The digital comparator A3 also receives an output from a fixed number switch A4. The output of the digital comparator A3 is connected to a counter A6 and an R/S flip-flop A9. Another oscillator A5 is also provided which has an output coupled to counters A6 and A13, and AND gates A10 and A11. The flip-flop A9 is reset by an output from a digital comparator A7. Another R/S flip-flop A16 is also provided which is reset by an output from a digital comparator A14 coupled to the counter A13. A control unit A17 is also coupled to the counter A13. The control unit A17 serves to activate the counter A13 in accordance with an operation of a manual infusion switch A12. The control unit A17 applies its output to the counters A13 and A16. The output from the control unit A17 is also sent to a counter A21. The output of the counter A21 is coupled to a digital comparator A22 which is, in turn, coupled to a step motor driver A19 for driving a step motor A20. The output of the flip-flop A16 is coupled to one input of the AND gate A11, which is also coupled at the other input thereof to the oscillator A5. The output of the AND gate A11 is coupled to one input of an OR gate A18. Fixed number switches A15 and A25 are connected to the digital comparators A14 and A22, respectively. Each of the fixed number switches A4, A8, A15, and A25 has five protruding insert bars and serves to provide a reference value for an associated one of the digital comparators A3, A7, A14, and A22. A light source A24 and a photo sensor A23 are coupled to the counter A21 in order to provide sensing results thereof to the counter A21, respectively. Referring to FIGS. 2 and 3, the arrangements of the light source A24 and photo sensor A23 are illustrated. As shown in FIGS. 2 and 3, the light source A24 and photo sensor A23 are arranged in such a fashion that they face each other while being vertically spaced from each other. A gear plate, which is included in a gear mechanism G, is interposed between the light source A24 and photo sensor A23. The gear plate has a plurality of through holes A26 uniformly spaced from one another in a circumferential direction, as shown in FIG. 3. The gear plate is fixedly fitted around a gear shaft A27 having a screw portion. A piston plate A28 is threadedly coupled to the gear shaft A27 in the form of a nut in such a fashion that it slides along the screw portion of the gear shaft A27 when the gear shaft A27 rotates. The rotation of the gear shaft A27 is carried out by a drive force from the motor A20 transmitted via the gear mechanism G. The driving of a motor M (corresponding to the motor A20 in FIG. 1) is controlled by the operations of the counter A21, digital comparator A22, switch A25, and motor drive A19. The above mentioned elements of the syringe device are received in a housing, as shown in FIG. 2. In particular, the light source A24 and photo sensor A23 are fixedly mounted at an upper portion of the housing by means of a bracket fixed to the housing. In this syringe device, a liquid medicine, such as insulin, contained in a syringe I is outwardly injected through an injection needle N connected to the syringe I, by a sliding movement of the piston plate A28. In such a syringe device, however, the housing and syringe I thereof are exposed to the atmosphere. As a result, moisture and water are likely to penetrate into the syringe device. For this reason, there is inconvenience in that if the user desires to take a shower while the syringe is in place, then the housing should be contained in a separate sealing case.

In order to solve such a problem, a sealable syringe device has been proposed by the applicant. Such a sealable syringe device is illustrated in FIG. 4, which is a front view. Referring to FIG. 4, the syringe device includes a cover 10 sealably coupled to the upper end of a housing 20, and a bottom cover 40 sealably coupled to the lower end of the housing 20. A connector 2, to which a feeding tube 1 is integrally connected, is threadedly coupled to the cover 10. The connector 2 communicates with a syringe 21 received in the housing 20. A piston 22 is slidably fitted in the syringe 21. A liquid medicine to be injected is contained in the syringe 21. A power transmission means 30 is mounted on the bottom surface of the housing 20. The power transmission means 30 has a rotating shaft 31 to which a disc type pushing means 50 is threadedly coupled. The disc type pushing means 50 moves vertically by a rotation of the rotating shaft 31, thereby vertically moving the piston 22.

Referring to FIG. 5, which is a plan view of FIG. 4, the cover 10, to which the connector 2 connected with the feeding tube 1 is connected, is arranged on the left portion of the upper surface of the housing 20. A battery cover 24 is arranged on the right portion of the upper surface of the housing 20.

FIG. 6 is a cross-sectional view taken along the line A—A of FIG. 5. As shown in FIG. 6, the cover 10 is centrally provided with a threaded hole 11 in which the connector 2 is threadedly fitted at its lower end. The threaded hole 11 has threads 11-1. The connector is formed, at its lower end, with threads 2-15 to be threadedly coupled with the threads 11-1 of the threaded hole 11. The cover 10 is also provided at its lower end with a bolt portion 12 threadedly fitted in the upper end of the housing 20. A packing 13 is fitted around the bolt portion 12 of the cover 10 between the lower end of the cover 10 and the upper end of the housing 20. A syringe receiving chamber 23 is defined in the interior of the housing 20. The pushing means 50 is fitted in the lower end of the housing 20 in such a fashion that it slides vertically in the housing 20. The housing 20 is also formed at its inner surface with a vertical pushing means guide groove 25 adapted to guide a vertical movement of the pushing means 50 and vertical piston guide grooves 27 adapted to guide a vertical movement of the piston 22.

FIG. 7 shows a detailed configuration of the power transmission means 30 mounted on the bottom surface of the housing 20 and a detailed configuration of the pushing means 50 threadedly coupled to the rotating shaft 31 of the power transmission means 30. As shown in FIG. 7, the pushing means 50 includes a lower disc 54 threadedly coupled to the rotating shaft 31 in such a fashion that it slides vertically along the rotating shaft 31. The lower disc 54 is provided at its periphery with a guide protrusion 51 engaged in the guide groove 25 of the housing 20 and adapted to guide the vertical movement of the lower disc 54. The pushing means 50 also includes an upper disc 55 integrally formed with the lower disc 54. The upper disc 55 is provided at its periphery with an engagement means 52. The upper disc 55 is fitted in a sleeve plate 26 (FIG. 8) fixed to the lower end of the piston 22 in such a manner that its engagement means 52 engages with a mating engagement means formed on the inner peripheral surface of the sleeve plate 26. The sleeve plate 26 is also provided at its outer peripheral surface with protrusions engaging with the guide grooves 27 respectively. The power transmission means 30 includes a reduction mechanism 33 for transmitting the rotational force of a motor (not shown) to the rotating shaft 31 in a speed-reduced manner.

In order to use the syringe device having the above mentioned configuration, the piston 22, which is in a state separated from the housing 20, is first fitted in the syringe 21, which is also in a state separated from the housing 20, in such a manner that it is completely inserted into the syringe 21. In this state, a disposable injection needle (not shown) is fitted onto the tip 21-1 of the syringe 21. Thereafter, the injection needle is penetrated into the interior of a phial through the plug of the phial. In this state, the piston 22 is pulled to suck a liquid medicine (for example, insulin) contained in the phial into the syringe 21.

The piston 22, which is in a state fitted in the syringe 21 containing the liquid medicine, is then inserted into the syringe receiving chamber 23 of the housing 20 in such a manner that it is seated on the pushing means 50. Subsequently, the cover 10 is threadedly coupled to the upper end of the syringe receiving chamber 23. The connector 2 is then threadedly fastened to the cover 10. As the connector 2 is threadedly fastened to the cover 10, it is fitted onto the syringe tip 21-1. Thus, the syringe 21 is maintained in a sealed state in the housing 20. When the motor (not shown) is operated under the above condition, the pushing means 50 moves upwardly, thereby upwardly pushing the piston 22. As a result, the liquid medicine contained in the syringe 21 is outwardly injected from the syringe 21. At this time, the upward movement of the pushing means 50 is accurately carried out because its guide protrusion 51 engages with the guide groove 25. Since respective protrusions of the sleeve plate 26 slide along the piston guide grooves 27 shown in FIG. 6, the upward movement of the piston 22 is also accurately carried out.

Meanwhile, FIG. 9 illustrates an example of a conventional injection needle unit for portable automatic syringe devices enabling a prolonged injection of a liquid medicine. As shown in FIG. 9, the injection needle unit includes a feeding tube 1, a "-" shaped straight injection needle member (called a "straight butterfly-shaped injection needle") 3 connected to one end of the feeding tube 1, and a connector 2 connected to a connector portion 20-5 of the housing 20.

In order to use such an injection needle unit, the user himself angularly penetrates the straight butterfly-shaped injection needle member 3 into his subcutaneous tissue while observing the penetration of the injection needle member 3 with the naked eye. The reason why the user observes the penetration of the injection needle member 3 with the naked eye is because the injection needle member 3 has a straight shape. However, such an observation is very uncomfortable. The straight butterfly-shaped injection needle member 3 is also likely to move within the subcutaneous tissue of the user because it penetrates the subcutaneous tissue of the user at an angle. In this case, the subcutaneous tissue may be damaged. In severe cases, blood may flow out of the subcutaneous tissue. The user may also feel a severe pain.

As mentioned above, the conventional injection needle unit has a drawback in that it is difficult to smoothly inject insulin because the injection needle member 3, which penetrates the subcutaneous tissue of the user at an angle, may be easily blocked at its tip by the subcutaneous tissue. To this end, the feeding tube of such a conventional injection needle unit inevitably has an increased diameter. However, such a feeding tube having an increased diameter results in a possibility of an excessive insulin injection. In addition, this may result in wastage of expensive insulin. For instance, where it is desired to inject insulin into the user using an automatic syringe device equipped with the above mentioned injection needle unit, it is necessary to completely vent air existing in the feeding tube 1 and injection needle member 3 before penetrating the injection needle member 3 into the subcutaneous tissue of the user. To this end, insulin, which is contained in the syringe device, is outwardly discharged through the feeding tube 1 and injection needle member 3, thereby venting air. In this case, a large amount of insulin is wasted where the conventional injection needle unit having the diameter-increased feeding tube is used.

In order to solve this problem, an injection needle unit has been proposed which has an L-shaped injection needle. Such an injection needle unit is illustrated in FIGS. 10 and 11, respectively. As shown in FIGS. 10 and 11, the injection needle unit includes a feeding tube 1, an injection needle member 3 connected to one end of the feeding tube 1, and a connector 2 connected to the other end of the feeding tube 1.

In the case of the injection needle unit shown in FIGS. 10 and 11, the injection needle member 3 has an injection needle 3-11 having an L-shaped structure shown in FIG. 12. This injection needle 3-11 has a first portion, namely, a horizontal portion, fitted in a connecting rib 3-12 integrally formed with one end of the feeding tube 1, and a second portion, namely, a vertical portion, provided with a needle tip. The injection needle 3-11 is provided with a curved portion 3-13 at its horizontal portion fitted in the connecting rib 3-12, as shown in FIG. 11. A pressing member 3-14 is integrally formed with the connecting rib 3-12 in such a fashion that the injection needle 3-11 protrudes perpendicularly from the pressing member 3-14. The pressing member 3-14 is pressed against the skin of the user upon penetrating the injection needle member 3 into the subcutaneous tissue. A bacterial infection prevention member 3-14-1, which is made of a sterile nonwoven fabric, is attached to the surface of the pressing member 3-14 which comes into contact with the skin of the user upon penetrating the injection needle unit 3 into the subcutaneous tissue. The connector 2, which is connected to the other end of the feeding tube 1, has a male thread 2-15. The connector 2 is protected by a protection cap 2-17 which has a female thread 2-16 threadedly coupled to the male thread 2-15 of the connector 2. In use, the connector 2 is threadedly coupled to a connector portion 20-5 of a housing 20 included in an automatic insulin syringe device. The connector portion 20-5 of the housing 20 has a female thread 20-5a threadedly coupled to the male thread 2-15 of the connector 2. In FIG. 10, the reference numeral "3-18" denotes a needle protection cap.

Where it is desired to inject insulin contained in the automatic insulin syringe device using the above mentioned injection needle unit, the protection cap 2-17 is first separated from the connector 2, which is, in turn, threadedly coupled to the connector portion 20-5 of the housing 20. Thereafter, the needle protection cap 3-18 is separated from the injection needle 3-11. The user then penetrates the injection needle 3-11 into the subcutaneous tissue while pressing the pressing member 3-14 against the skin by hand. At this time, the injection needle 3-11 penetrates vertically into the subcutaneous tissue of the user because it has an "L" shape. Accordingly, the user can carry out the penetration of the injection needle 3-11 instantaneously without having to observe the penetration with the naked eye. Therefore, the user feels little pain upon penetrating the injection-needle 3-11 into the subcutaneous tissue. By virtue of such a configuration of the injection needle unit 3, the automatic insulin syringe device can be conveniently used, as shown in FIG. 13. Since the injection needle 3-11 penetrates vertically into the subcutaneous tissue of the user by virtue of its "L" shape, there does not occur any phenomenon that the injection needle 3-11 is blocked at its tip by the subcutaneous tissue of the user. Thus, the injection of insulin is smoothly carried out. Accordingly, the feeding tube can have a reduced diameter and an increased length. Since the feeding tube 1 has a reduced diameter, it is possible to minimize the wastage of insulin occurring upon venting air existing in the feeding tube 1 and injection needle 3-11 and to reduce the manufacturing costs. Since the feeding tube 1 also has an increased length, it is possible to extend the range of the applied positions of the injection needle 3-11 on the body of the user. Accordingly, it is possible to achieve convenience in use. Since the bacterial infection prevention member 3-14-1, which is made of a sterile nonwoven fabric, is attached to the pressing member 3-14, it is possible to prevent the pressing member 3-14 from coming into direct contact with the skin of the user upon penetrating the injection needle unit 3 into the subcutaneous tissue. Accordingly, it is possible to prevent the user from being infected. Since the injection needle 3-11 penetrates vertically into the subcutaneous tissue of the user by virtue of its "L" shape, as mentioned above, it hardly moves in the subcutaneous tissue, even when an external force is applied thereto. Accordingly, there is no damage caused to the subcutaneous tissue. Of course, there does not occur any phenomenon that blood flows out of the subcutaneous tissue. The user also does not feel any pain.

In the case of the injection needle unit mentioned above, the needle protection cap 3-18 is used which has a configuration as shown in FIG. 14. The needle protection cap 3-18 has a needle tip receiving hole including a smaller diameter portion 3-18-1 with the same diameter as the injection needle 3-11 and a larger diameter portion 3-18-2 with a diameter larger than the diameter of the injection needle 3-11. Since the needle protection cap 3-18 has such a configuration, there is a problem in that it is difficult to separate the needle protection cap 3-18 from the injection needle 3-11 because of the small diameter of the smaller diameter portion 3-18-1. As a result, the injection needle 3-11 may be damaged. Since the smaller diameter portion 3-18-1 has a small diameter, a capillary phenomenon may occur between the inner surface of the needle protection cap 3-18 and the outer surface of the injection needle 3-11 when the liquid medicine is outwardly discharged from the injection needle 3-11 to vent air existing in the feeding tube 1 and injection needle 3-11. In this case, a part of the discharged liquid medicine is absorbed in the bacterial infection prevention member 3-14-1, thereby causing the user to be uncomfortable. The injection needle 3-11 has a sharply bent portion 3-11-1 between the vertical and horizontal portions thereof due to its "L"-shaped structure. This sharply bent portion 3-11-1 of the injection needle 3-11 may be subjected to excessive stress when the user moves excessively during injection. For instance, when the needle tip of the injection needle 3-11 moves from a position indicated by the solid line of FIG. 15 to a position indicated by the phantom line of FIG. 15 as the user exercises or conducts hard work, or due to other reasons, the sharply bent portion 3-11-1 of the injection needle 3-11 may be subjected to excessive stress. In this case, the injection needle 3-11 may be broken. For this reason, the reliability of the above mentioned injection needle unit is degraded.

In order to solve such a problem, a portable automatic syringe device has been proposed which has a configuration including a separable rotating shaft adapted to provide a drive force to a piston included in the automatic syringe device so that the rotating shaft can be separated, along with the piston, from a housing of the syringe device upon re-filling a syringe of the syringe device with a liquid medicine, and set in position in the housing, after the re-filling of the liquid medicine, while observing the setting operation with the naked eye. FIG. 16 is a perspective view illustrating an example of such a portable automatic syringe device. As shown in FIG. 16, the syringe device includes a housing 120, a syringe 21 separately received in the housing 120, a piston 122 slidably fitted in the syringe 21 and separately received in the housing 120, a piston pushing means 150 received in the housing 120 and adapted to vertically move the piston 122, a power transmission means 130 received in the housing 120 and adapted to generate a drive force, and a rotating shaft 131 received in the housing 120 and adapted to drive the piston pushing means 150 by the drive force transmitted from the power transmission means 130. The syringe device also includes an injection needle unit (in FIG. 16, only its feeding tube 1 and connector 2 are shown). The injection needle unit is connected to the housing 120 by means of a cover 110 which is sealably coupled to the upper end of the housing 120 at one side of the housing 120. A control button unit 123 is also installed on the housing 120. The control button unit 123 is electrically connected to a control circuit (not shown) installed in the housing 120 to control the power transmission means 130. A display 124 such as an LCD is also installed on the housing 120 in order to display the operating state of the syringe device. At the other side of the housing 120, a battery cover 125 is separately coupled to the upper end of the housing 120 in order to carry a battery in the housing 120. A reset button 121 is also installed on the housing 120 to generate a reset signal for the control circuit. In FIG. 16, the reference numeral "140" is a bottom cover.

Referring to FIG. 17, which is a plan view of FIG. 16, the cover 110 and battery cover 125 are arranged at opposite sides of the upper wall of the housing 120, respectively. The reset button 121 is arranged on the upper wall of the housing 120 between the covers 110 and 125.

FIG. 18 is a plan view similar to FIG. 17, but without the cover 110. FIG. 18 illustrates the inner construction of the housing 120 in which the piston 122 and piston pushing means 150 are received. FIG. 19 is a cross-sectional view taken along the line B—B of FIG. 18. As shown in FIG. 19, the housing 120 has a syringe receiving chamber 126 defined in the interior of the housing 120. At the lower end of the syringe receiving chamber 126, the housing 120 has a hollow support portion in which a coupling member 132 coupled to the power transmission means 130 is rotatably fitted. The housing 120 is also formed, at its inner surface defining the syringe receiving chamber 126, with a vertical pushing means guide groove 25 adapted to guide a vertical movement of the pushing means 150 and vertical piston guide grooves 27 adapted to guide a vertical movement of the piston 122.

FIG. 20 is an enlarged perspective view illustrating the configuration of the coupling member 132 to which the rotating shaft 131 is coupled. As mentioned above, the coupling member 132 is rotatably fitted in the hollow support portion of the housing 120 at the lower end of the syringe receiving chamber 126. As shown in FIG. 20, the coupling member 132 has a cross groove 132-1 in which a horizontal engaging pin 133 coupled to the lower end of the rotating shaft 131 is separately engaged. A gear 132-3 is also integrally formed with the coupling member 132. The gear 132-3 engages with an output gear of the power transmission means 130. Both ends of the engaging pin 133 are protruded from opposite sides of the lower end of the rotating shaft 131, respectively. By such a configuration, the coupling member 132 rotates by a drive force transmitted from the power transmission means 130 via the gear 132-3, thereby causing the rotating shaft 131 to rotate.

FIG. 21 is an exploded perspective view illustrating the rotating shaft 131, piston pushing means 150, piston 122, and syringe 21 separated from one another. FIG. 22 is a cross-sectional view illustrating the coupled state of the elements of FIG. 21. As shown in FIGS. 21 and 22, the rotating shaft 131 has a screw extending throughout the length thereof. A cap type head 131-1 is threadedly coupled to the upper end of the rotating shaft 131. The piston pushing means 150 is threadedly coupled to the rotating shaft 131 in such a fashion that it moves vertically along the rotating shaft 131. The piston pushing means 150 includes a push plate 154 threadedly coupled to the rotating shaft 131 in the form of a nut in such a fashion that it slides vertically along the rotating shaft 131. The push plate 154 is provided at its periphery with a radially-extending guide protrusion 151 engaged in the guide groove 25 of the housing 120 and adapted to guide the vertical movement of the push plate 154. The push plate 154 is also provided at its upper end with engaging protrusions 151-1. The piston pushing means 150 also includes a fitting member 155 extending upwardly from the push plate 154. The fitting member 155 is fitted into the lower end of the piston 122 which is open. An annular snap ring groove 156 is formed on the outer surface of the fitting member 155. The piston 122 has, at its lower portion, a snap ring 122-4 engaging with the snap ring groove 156. The piston 122 is also provided at its lower end with a radially-extending flange 122-1. A pair of radially-extending protrusions 122-2 are formed on the periphery of the flange 122-1. When the piston 122 is received in the syringe receiving chamber 126, the protrusions 122-2 engage with the guide grooves 27 of the housing 120, respectively, thereby guiding the vertical movement of the piston 122. A plurality of engaging grooves 122-3 are formed on the lower surface of the flange 122-1. When the piston pushing means 150 is fitted into the lower end of the piston 122, the engaging protrusions 151-1 thereof engage with optional ones of the engaging grooves 122-3 of the piston 122.

FIG. 23 is a cross-sectional view illustrating the reset button 121 installed on the housing 120. The reset button 121 is slidably fitted in a hole defined in the upper wall of the housing 120 in such a manner that it is separated from the hole. The reset button 121 is upwardly biased by a compression coil spring so that its upper end is in a state protruded from the hole of the housing 120. At least one packing seal 121-1 is fitted around the reset button 121 to provide a sealing effect between the housing 120 and reset button 121.

FIG. 24 is a block diagram illustrating a control circuit for the above mentioned syringe device. As shown in FIG. 24, the control circuit includes the control button unit 123 for generating a control signal adapted to select a desired control function, a control unit 170 provided with functions of a microcomputer and adapted to carry out a control operation in response to the control signal generated from the control button unit 123, a display unit 124 adapted to display data outputted from the control unit 170, a ROM 165 adapted to store a variety of data and programs, a motor drive unit 167 adapted to drive a motor 168 under the control of the control unit 170, and a photocoupler 169 adapted to sense a rotation of the motor 168. The rotation of the motor 168 is controlled by the motor drive unit 167. Preferably, the control unit 70 includes a pair of controllers, that is, a first controller 171 and a second controller 172, which have the same function, in order to maintain a desired function even when one of the controllers 171 and 172 is out of order. The controllers 171 and 172 have terminals P1 to P5 and terminals P1' and P2', respectively. These terminals are ports connected to data and/or bus lines, respectively. For the motor 168, a stepping motor or servo motor may be used.

Now, the syringe device having the above mentioned configuration will be described.

First, the push plate 154 of the piston pushing means 150 is threadedly coupled to the rotating shaft 131 in such a manner that it is disposed at the middle portion of the rotating shaft 131. Thereafter, the engaging pin 133 is coupled to the lower end of the rotating shaft 131. Also, the cap type head 131-1 is threadedly coupled to the upper end of the rotating shaft 131. The rotating shaft 131 is then inserted into the lower end of the piston 122 until the fitting member 155 of the piston pushing means 150 is fitted in the lower end of the piston 122. In this state, the snap ring groove 156a of the fitting member 155 engages with the snap ring 122-4 of the piston 122. Also, the engaging protrusions 151-1 of the push plate 154 engage with optional ones of the engaging grooves 122-3 of the piston 122. The piston 122, which is coupled to the rotating shaft 131, is then fitted in the syringe 21 in such a manner that it is completely inserted into the syringe 21, as indicated by the double-dotted line in FIG. 22. In the illustrated case, the engaging grooves 122-3 have a small pitch to have the form of gear teeth whereas the protrusions 151-1 have a large pitch. In this case, it is possible to achieve an easy assembling process. In order to achieve an easier assembling process, the guide protrusions 122-2 of the piston 122 may be eliminated, thereby eliminating the reference position of the piston 122 upon assembling the piston 122. Of course, the provision of the guide protrusions 122-2 provides an advantage in that the piston 122 operates more accurately. In this state, a disposable injection needle (not shown) is fitted onto the tip of the syringe 21. Thereafter, the injection needle is penetrated into the interior of a phial through the plug of the phial. In this state, the piston 122 is pulled, along with the rotating shaft 131, to suck a liquid medicine contained in the phial into the syringe 21, as indicated by the solid line in FIG. 22. In order to allow the engaging pin 133 of the rotating shaft 131 to be accurately engaged in the cross groove 132-1 of the coupling member 132 when the syringe 21 filled with the liquid medicine is inserted into the syringe receiving chamber 126 of the housing 120, it is necessary to appropriately adjust an initial length of the rotating shaft 131 protruded from the piston 122 in accordance with the amount of the liquid medicine contained in the syringe 21. In order to achieve an easy and convenient adjustment of the initial protruded length of the rotating shaft 131, a scale (not shown) may be formed on the housing 120. Alternatively, a mark (not shown) indicative of a reference position for the rotating shaft 131 may be formed on the housing 120. Otherwise, a length measuring jig may be used. In this state, the syringe 21, in which the piston 122 is fitted, is inserted into the syringe receiving chamber 126 of the housing 120 in such a manner that the engaging pin 133 of the rotating shaft 131 is engaged in the cross groove 132-1 of the coupling member 132, as indicated by the arrow in FIG. 20. When the motor (not shown) drives under the above condition, its drive force is transmitted to the gear 132-3 via the power transmission means 130. Accordingly, the coupling member 132 integral with the gear 132-3 rotates. The rotation of the rotating shaft 131 is carried out in a speed-reduced manner because the drive force of the motor is transmitted via the power transmission means 130. When the rotating shaft 131 rotates, the pushing means 50 moves vertically because the guide protrusion 151 of the push plate 154 is engaged in the guide groove 25 of the housing 120.

The rotation of the coupling member 132 results in a rotation of the rotating shaft 131 because the engaging pin 133 of the rotating shaft 131 is engaged in the cross groove 132-1 of the coupling member 132. For example, when the rotating shaft 131 rotates counter-clockwise, as shown in FIG. 22, the push plate 154 moves upwardly while being guided by the guide groove 25. As a result, the piston 122 coupled to the push plate 154 moves upwardly. Accordingly, the liquid medicine contained in the syringe 21 is injected into the body of the user, into whom the injection needle of the injection needle unit through the connector 2 penetrates, via the connector 2 and feeding tube 1. As the injection of the liquid medicine is carried out for a prolonged time, the piston 122 reaches its initial position indicated by the double-dotted line in FIG. 22. In this state, the user separates the injection needle unit from the body and completes the use of the syringe device. Thereafter, the connector 2 of the injection needle unit is separated from the cover 110 which is, in turn, released from the housing 120. The syringe 21, piston 122, pushing means 150 and rotating shaft 131 assembled together are removed from the syringe receiving chamber 126 of the housing 120. Where it is desired to use again the syringe device, a liquid medicine is filled in the syringe 21 in accordance with the above mentioned piston function. Thereafter, the user rotates the rotating shaft 131 by hand so that the rotating shaft 131 is inserted into the piston 122 to its original position. That is, the rotating shaft 131 is adjusted to have a desired initial length protruded from the piston 122. In order to achieve an easy adjustment of the initial protruded length of the rotating shaft 131, it may be possible to use a scale formed on the housing 120, a mark indicative of a reference position for the rotating shaft 131 formed on the housing 120, or a length measuring jig. As mentioned above, the reason why the rotating shaft 131 is adjusted to have a desired initial length protruded from the piston 122 is to allow the engaging pin 133 of the rotating shaft 131 to be accurately engaged in the cross groove 132-1 of the coupling member 132 when the syringe 21 is fitted in the syringe receiving chamber 126 of the housing 120. Once the push plate 154 is threadedly coupled to the rotating shaft 131, it is prevented from being separated from the rotating shaft 131 because the cap type head 131-1 is threadedly coupled to the upper end of the rotating shaft 131. Accordingly, an improvement in durability is obtained. Where the injection of the liquid medicine contained in the syringe 21 is achieved by an upward movement of the piston 122 resulting from an upward movement of the pushing means 150 along the rotating shaft 131, it is necessary to return the upwardly-moved pushing means 150 to its initial position after refilling the syringe 21 with a liquid medicine to inject again the liquid medicine. However, it is disadvantageous to return the pushing means 150 to its initial position by reversely rotating the rotating shaft 131 using a drive force from the motor. This is because the drive force from the motor is transmitted to the rotating shaft 131 in a speed-reduced manner, so that a lengthy time of about 5 to 10 minutes is consumed for the pushing means to return to its initial position. In this case, accordingly, there is a wastage of time. In order to solve this problem, the rotating shaft 131 is configured to be separable from the motor so that it is manually rotated. Accordingly, it is possible to easily adjust the initial position of the pushing means by a manual rotation of the rotating shaft 131. The rotating shaft 131 is also configured to be rotated only in one direction by a drive force from the motor. Accordingly, the control of the motor is simplified. This results in a reduction in the manufacturing costs. In particular, all of the cover 110, battery cover 125, reset button 121 and bottom cover 140 are sealably configured, even though such a configuration is omitted from the drawings because it is well known. In this case, a vacuum is generated in the interior of the housing 120 as the liquid medicine contained in the syringe 21 is injected into the body of the user. As a result, the piston 122 is overloaded. This problem may be eliminated by forming the reset button 121 using a well-known semi-permeable material preventing penetration of moisture while allowing ventilation of air. In this case, it is possible to prevent a vacuum from being generated in the interior of the housing 120 while still maintaining a moisture sealing effect between the housing 120 and reset button 121. An increase in the manufacturing costs is incurred when the entire portion of the housing 120 is made of the semi-permeable material. However, where a small part of the housing 120, for example, the reset button 121, is made of the semi-permeable material, it is possible to minimize an increase in the manufacturing costs while maintaining an air-permeable effect for the housing 120 and providing convenience in installation. In this case, preferably, at least one packing seal 121-1 is fitted around the reset button 121 to provide a desired sealing effect between the housing 120 and reset button 121.

However, such an automatic syringe device performs only the automatic injecting function. Where a diabetic patient uses such a syringe device, there is inconvenience in that the patient has to separately measure his blood sugar level. Also, the doctor should periodically measure the blood sugar level of the patient using a separate blood sugar meter to regulate the quantity of insulin to be dispensed to the patient, based on the measured blood sugar level, resulting in inconvenience to both doctor and patient. Furthermore, the monitoring by the blood sugar meter may be subject to a time error. As a result, it may be difficult to accurately measure the blood sugar level of the patient at a precisely defined time.

SUMMARY OF THE INVENTION

The present invention has been made in view of the above mentioned problems, and an object of the invention is to provide a portable automatic syringe device capable of displaying the quantity of insulin dispensed to the user and the blood sugar level of the patient measured thereby, while having an automatic insulin injecting function.

In accordance with the present invention, this object is accomplished by providing a portable automatic insulin syringe device adapted to enable an injection of liquid medicine for a prolonged time, comprising a syringe pump having a pump housing, comprising: a blood sugar measuring unit mounted at one side of the pump housing and adapted to measure a blood sugar level of a user; a control unit for controlling the blood sugar measuring unit and the syringe pump; and a display unit for simultaneously displaying the quantity of insulin dispensed to a user and the blood sugar level measured by the blood sugar measuring unit.

The blood sugar measuring unit may comprise a housing having a lamp hole and an insert hole, a control panel adapted to control a measuring lamp and to convert a measured value from the measuring lamp into a signal capable of being recognized by the control unit, the measuring lamp received in the lamp hole while being outwardly exposed through the lamp hole, a measuring probe fitted in the insert hole, and a fitting protrusion member mounted to the housing in a spring-loaded state and adapted to maintain the measuring probe in a fitted state thereof.

BRIEF DESCRIPTION OF THE DRAWINGS

Other objects and aspects of the invention will become apparent from the following description of embodiments with reference to the accompanying drawings in which.

DESCRIPTION OF THE PREFERRED EMBODIMENTS

Now, the present invention will be described in detail, with reference to the annexed drawings.

Figure 1:
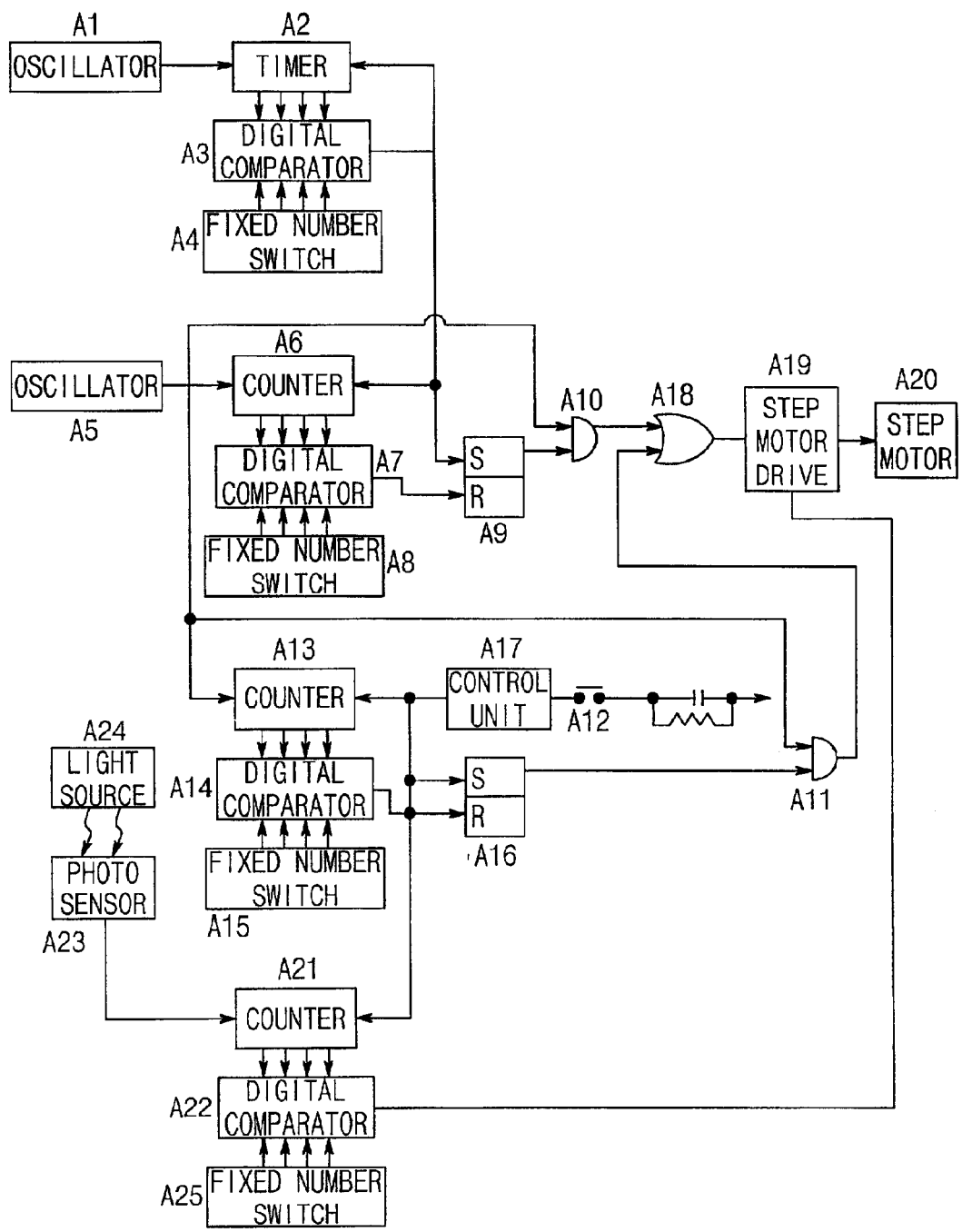
FIG. 1 is a block diagram illustrating a control circuit used in a conventional automatic syringe device.
Figure 2:
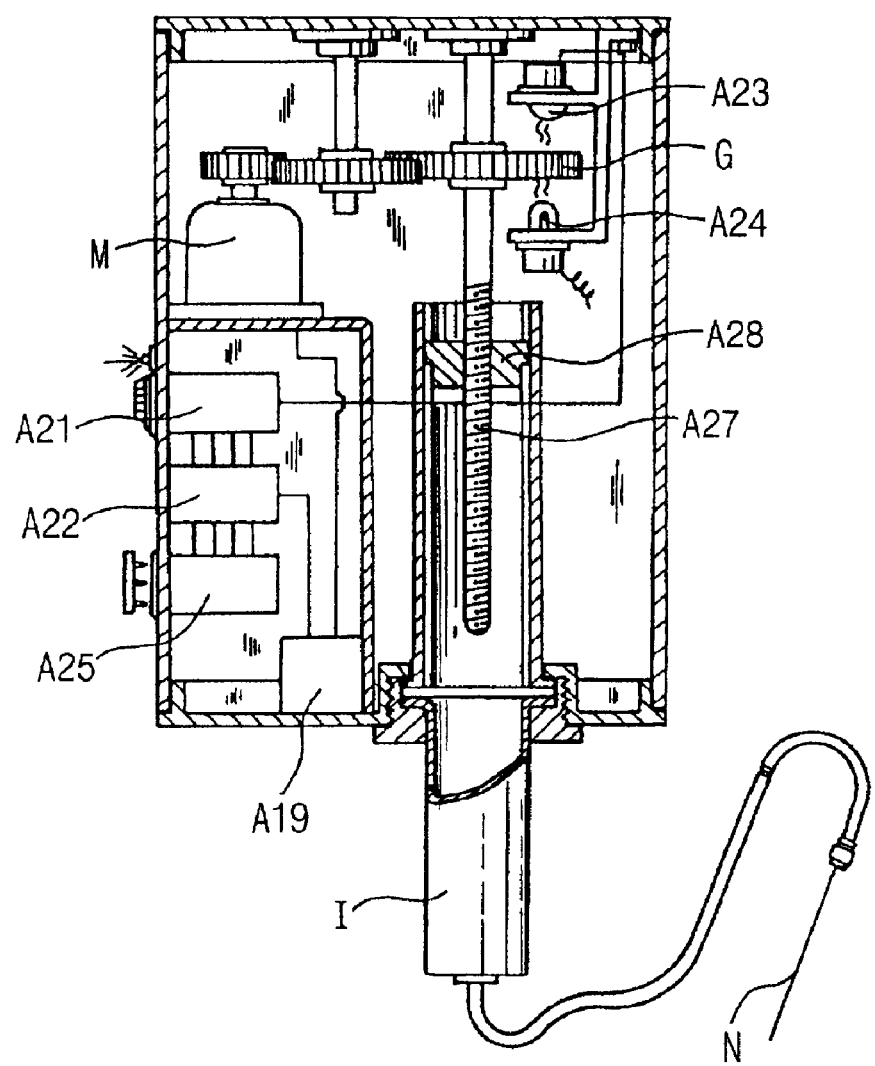
FIG. 2 is a cross-sectional view illustrating a structure of the automatic syringe device shown in FIG. 1.
Figure 3:
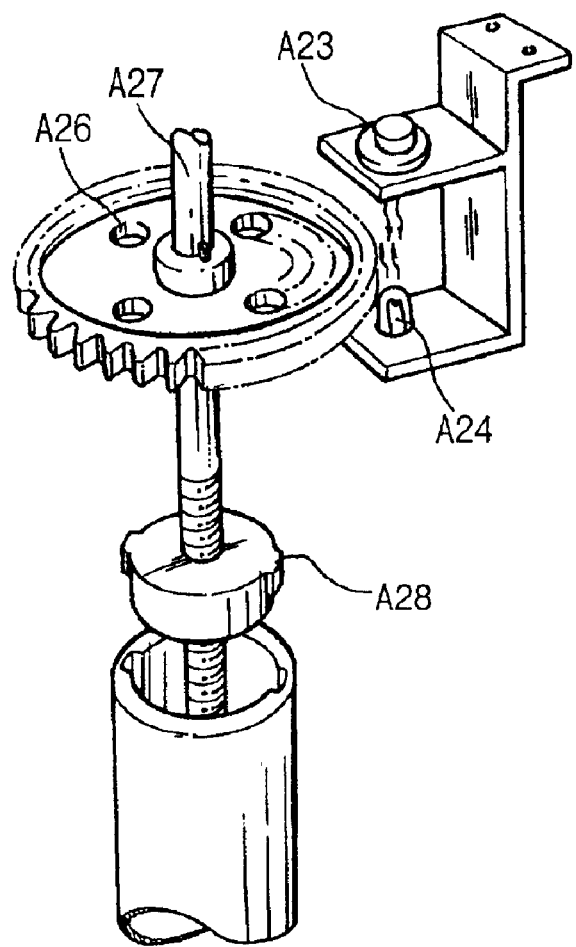
FIG. 3 is a perspective view illustrating the installation of a photo sensor in the automatic syringe device shown in FIG. 1.
Figure 4:
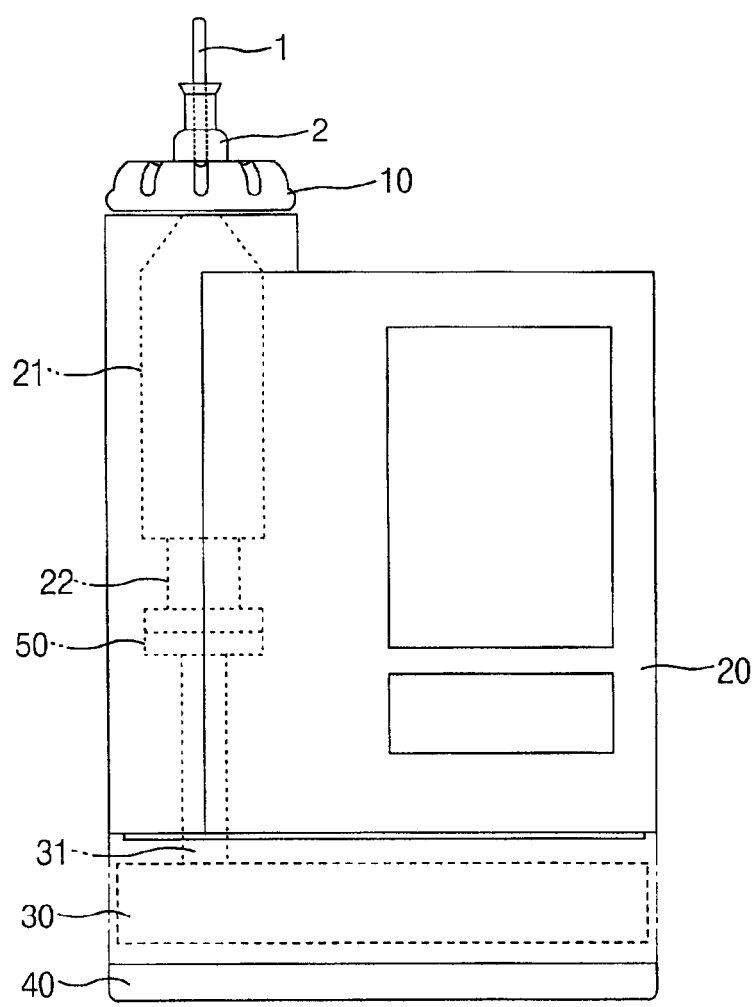
FIG. 4 is a front view illustrating another conventional automatic syringe device.
Figure 5:
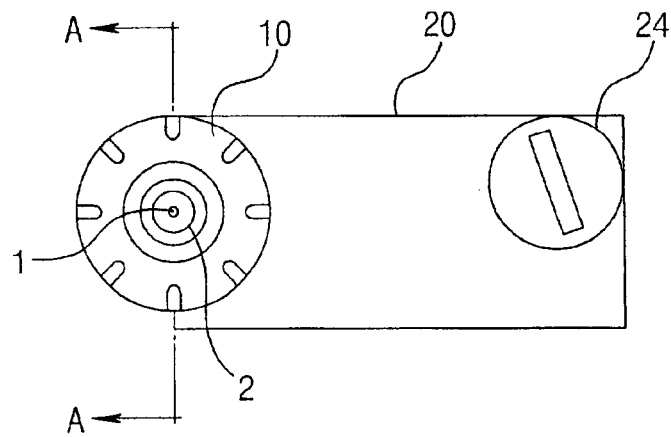
FIG. 5 is a plan view of FIG. 4.
Figure 6:
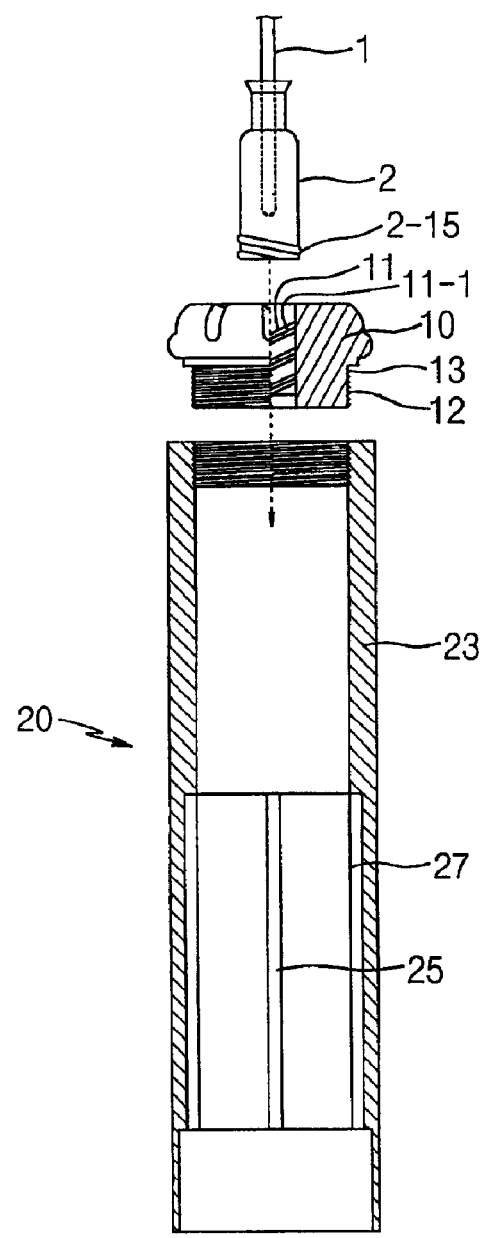
FIG. 6 is a cross-sectional view taken along the line A—A of FIG. 2.
Figure 7:
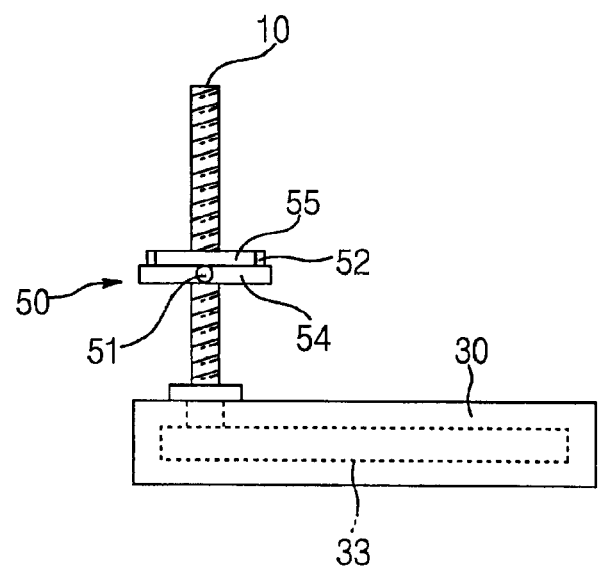
FIG. 7 is a view illustrating a conventional power transmission means.
Figure 8:
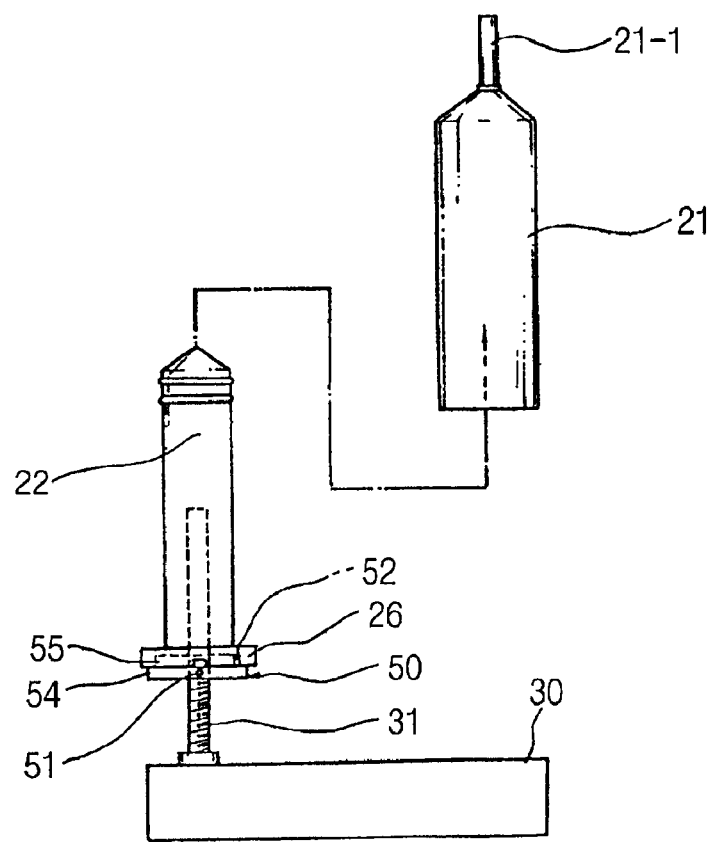
FIG. 8 is an exploded view illustrating a conventional pushing means.
Figure 9:
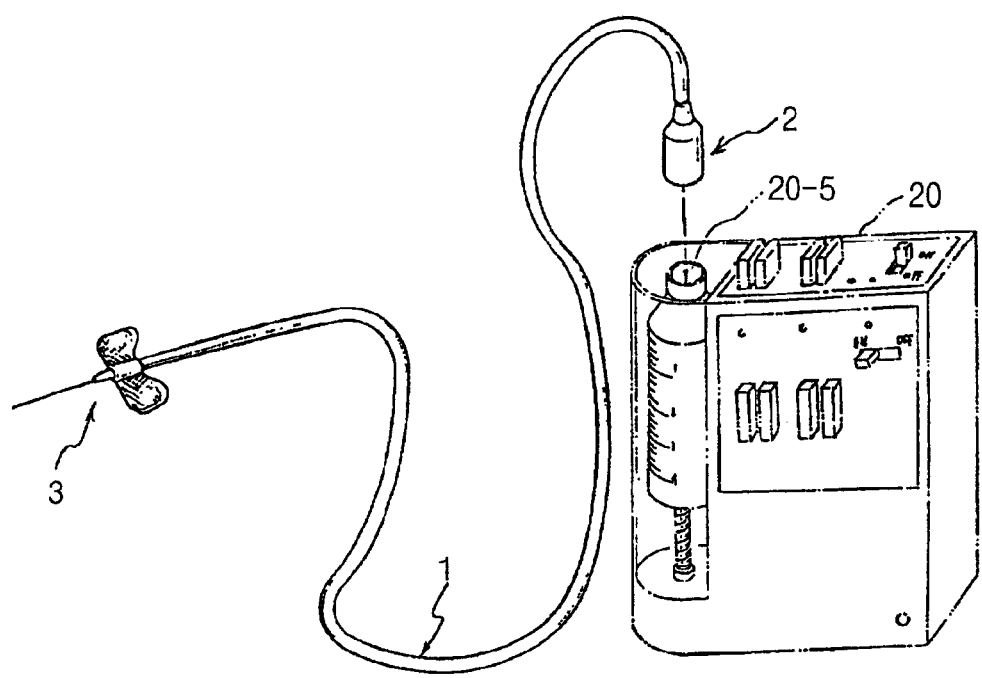
FIG. 9 is a perspective view illustrating an example of a conventional injection needle unit used for portable automatic syringe devices.
Figure 10:
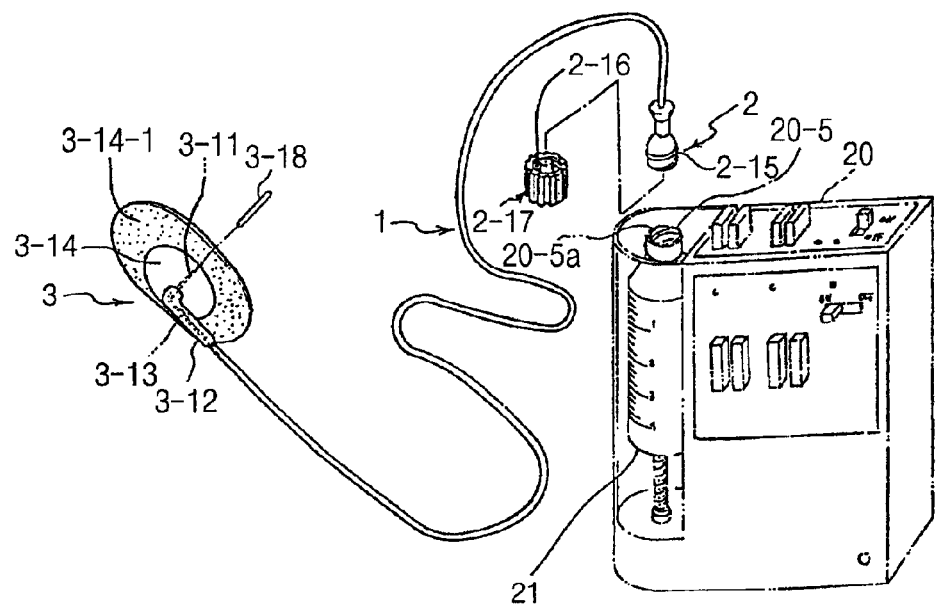
FIG. 10 is a perspective view illustrating another conventional injection needle unit.
Figure 11:
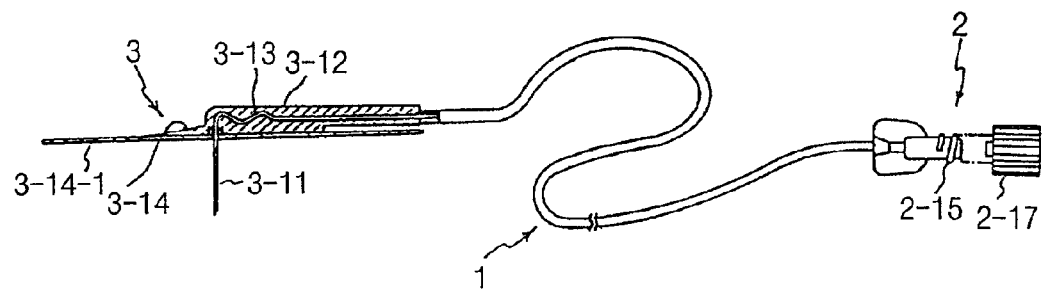
FIG. 11 is a partially-broken plan view illustrating the injection needle unit of FIG. 10.
Figure 12:
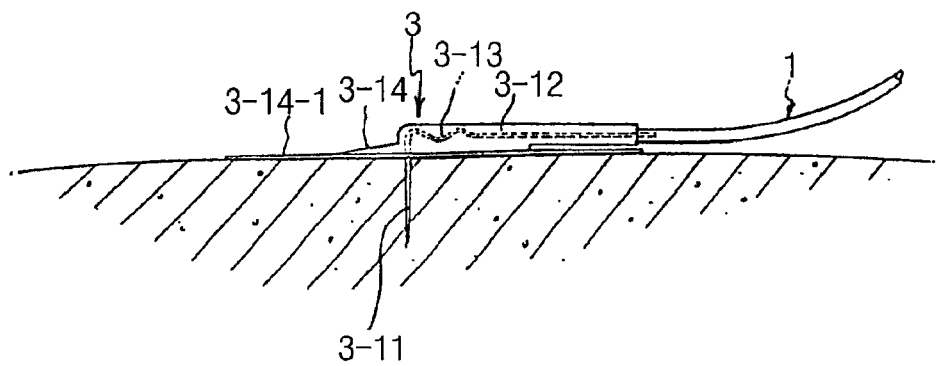
FIG. 12 is an enlarged view illustrating a using condition of the injection needle unit of FIG. 10.
Figure 13:
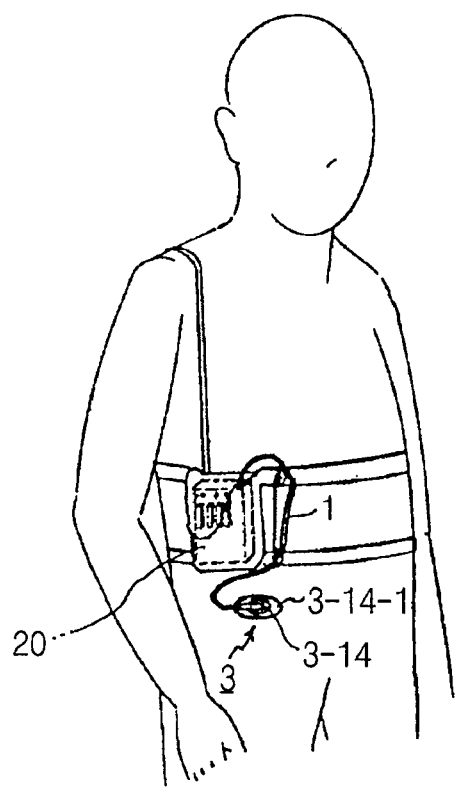
FIG. 13 is a perspective view illustrating a using condition of the injection needle unit of FIG. 10.
Figure 14:
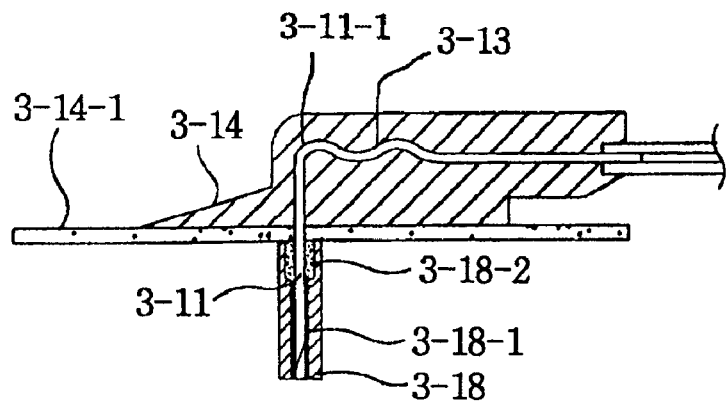
FIG. 14 is an enlarged view illustrating a part of the injection needle unit of FIG. 10.
Figure 15:
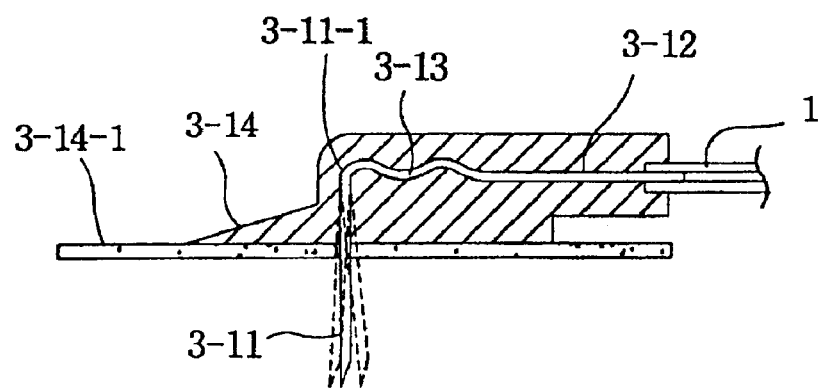
FIG. 15 is a view illustrating a drawback occurring when the injection needle unit of FIG. 10 is used.
Figure 16:
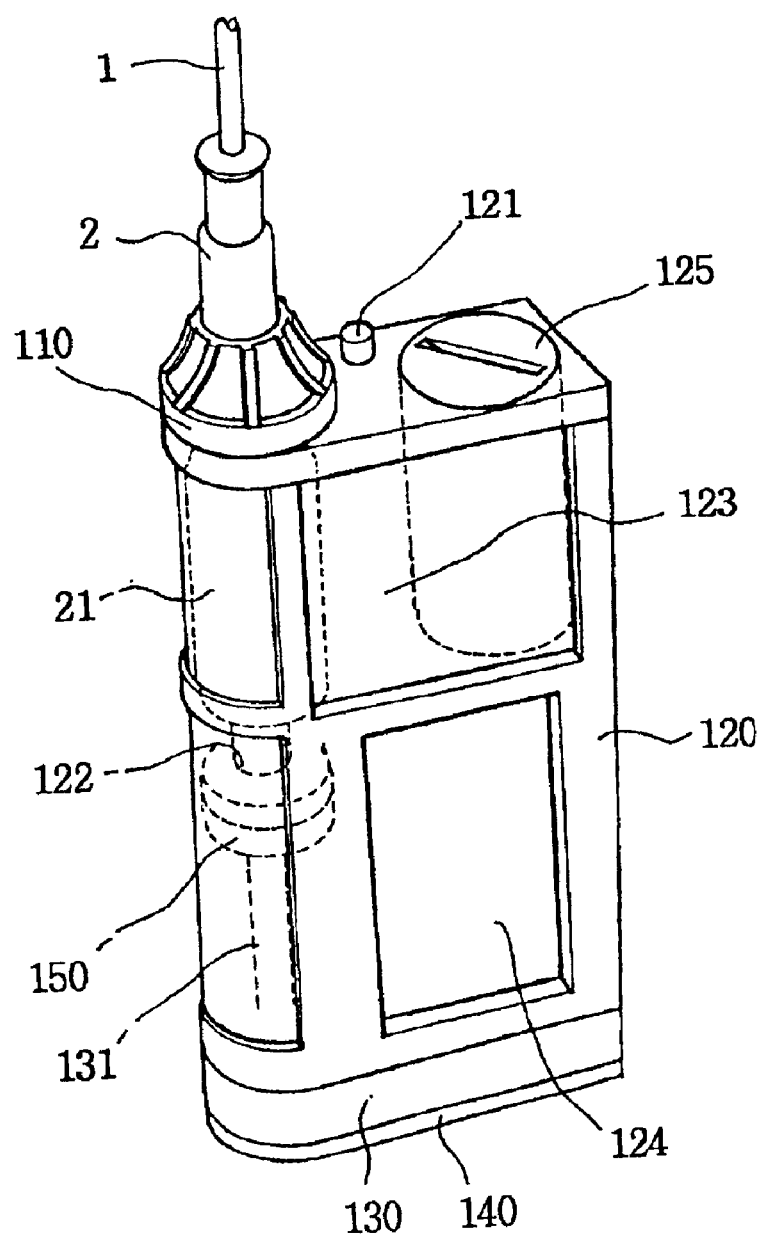
FIG. 16 is a perspective view illustrating a portable automatic syringe device according to an embodiment of the present invention.
Figure 17:
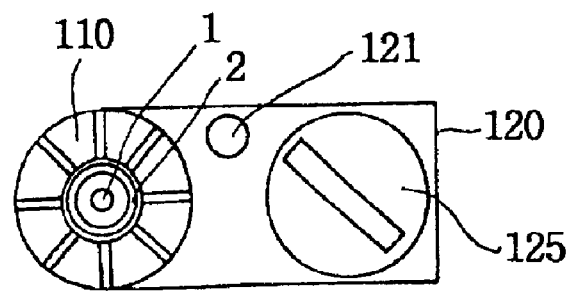
FIG. 17 is a plan view of FIG. 16.
Figure 18:
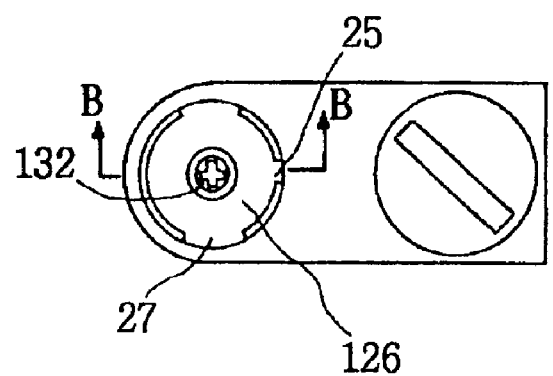
FIG. 18 is a plan view similar to FIG. 17, but eliminating a cover.
Figure 19:
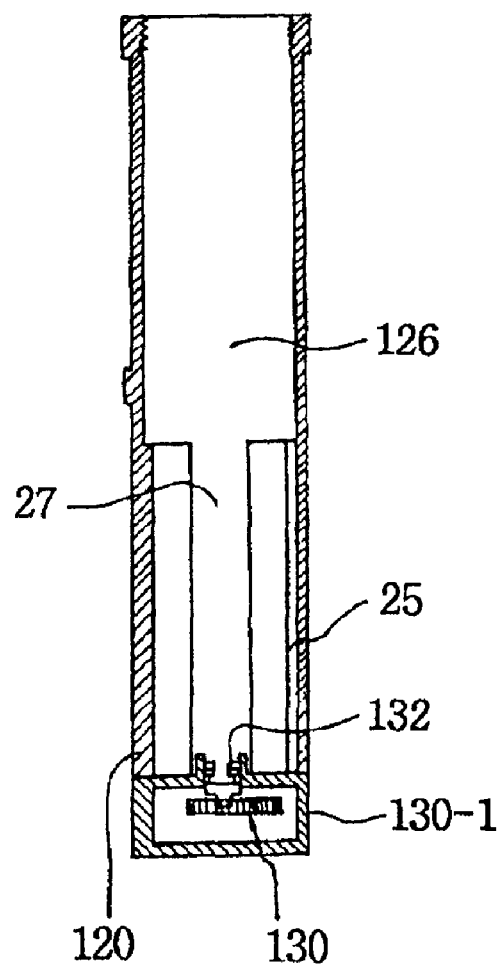
FIG. 19 is a cross-sectional view taken along the line B—B of FIG. 18.
Figure 20:
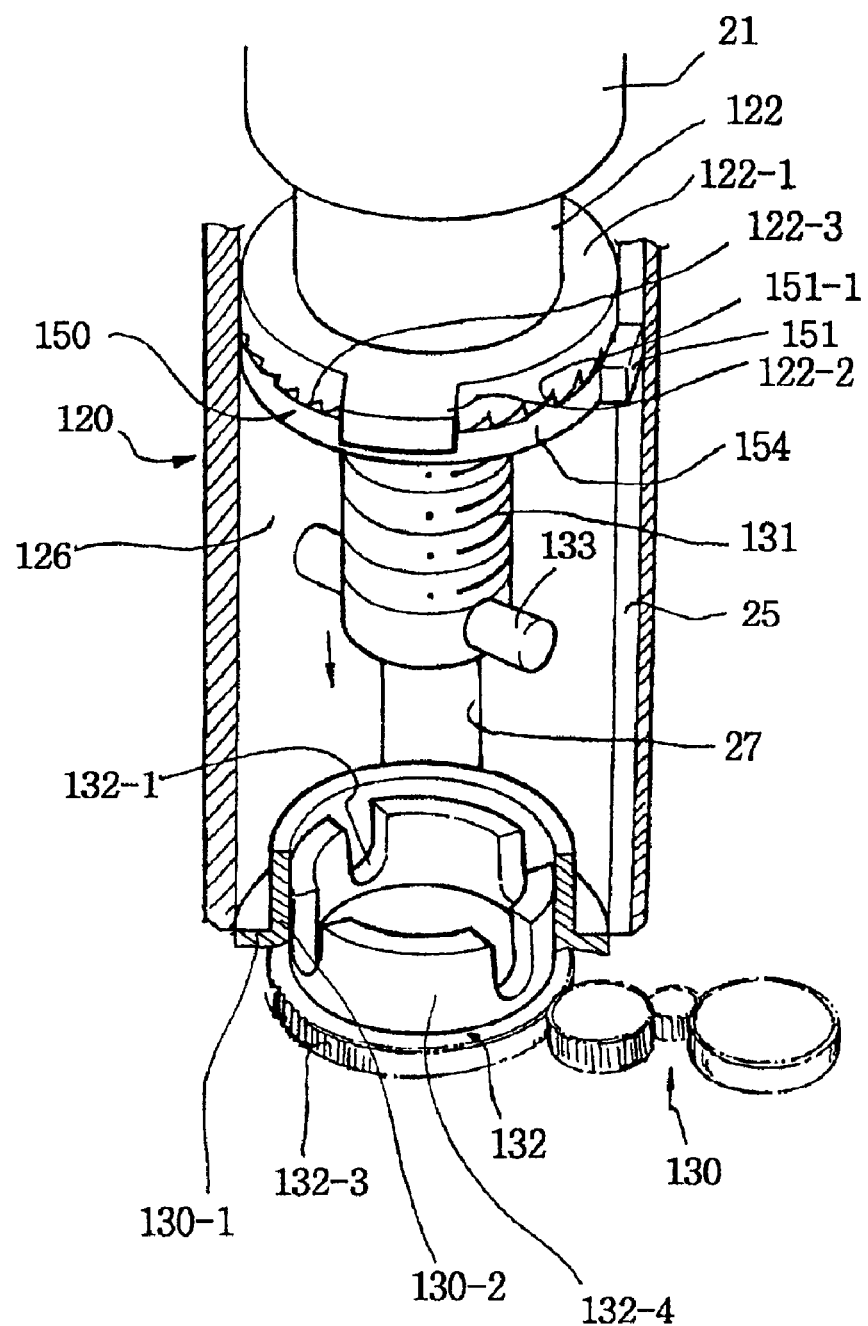
FIG. 20. is an enlarged perspective view illustrating a part of the automatic syringe device of FIG. 16.
Figure 21:
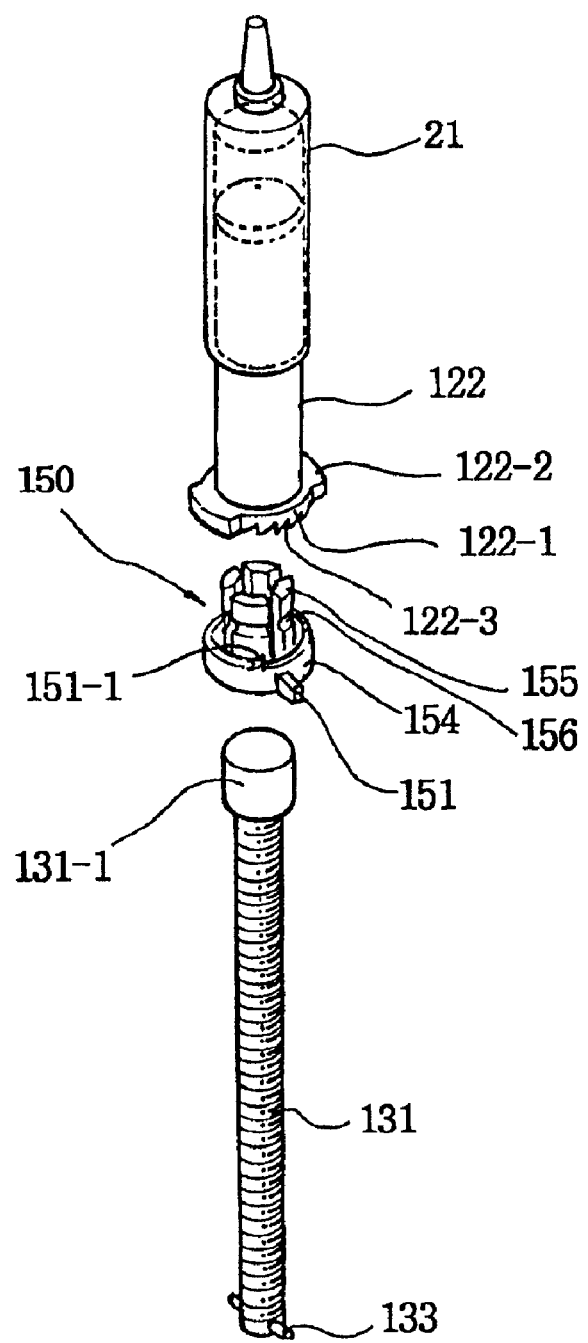
FIG. 21 is an enlarged perspective view illustrating a part of the automatic syringe device of FIG. 16.
Figure 22:
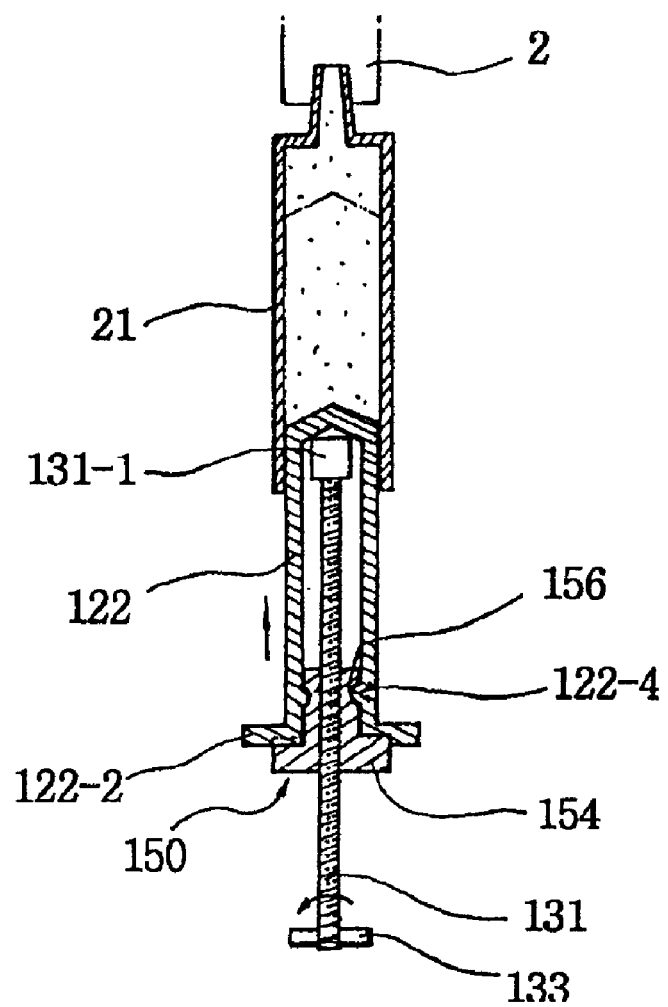
FIG. 22 is a cross-sectional view illustrating the coupled state of the elements of FIG. 21.
Figure 23:
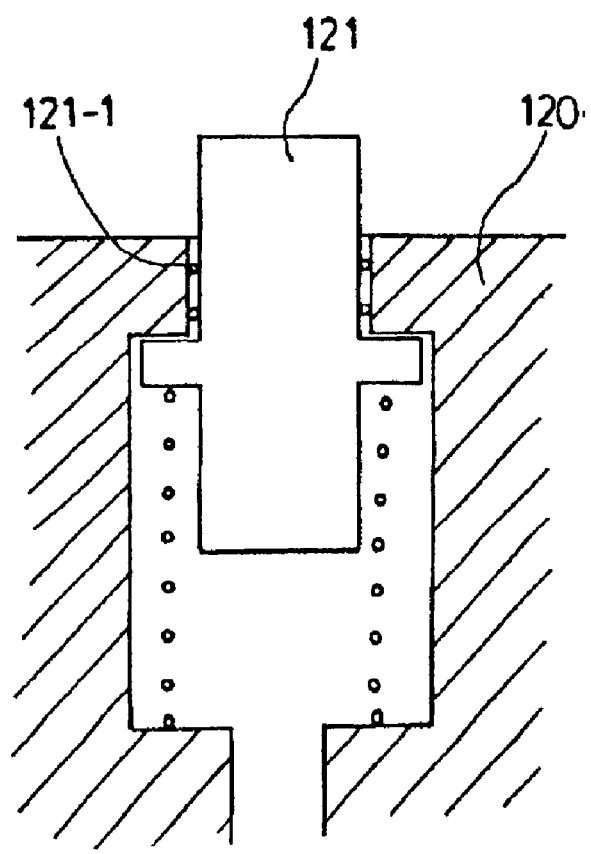
FIG. 23 is an enlarged cross-sectional view illustrating a reset button installed in accordance with the present invention.
Figure 24:
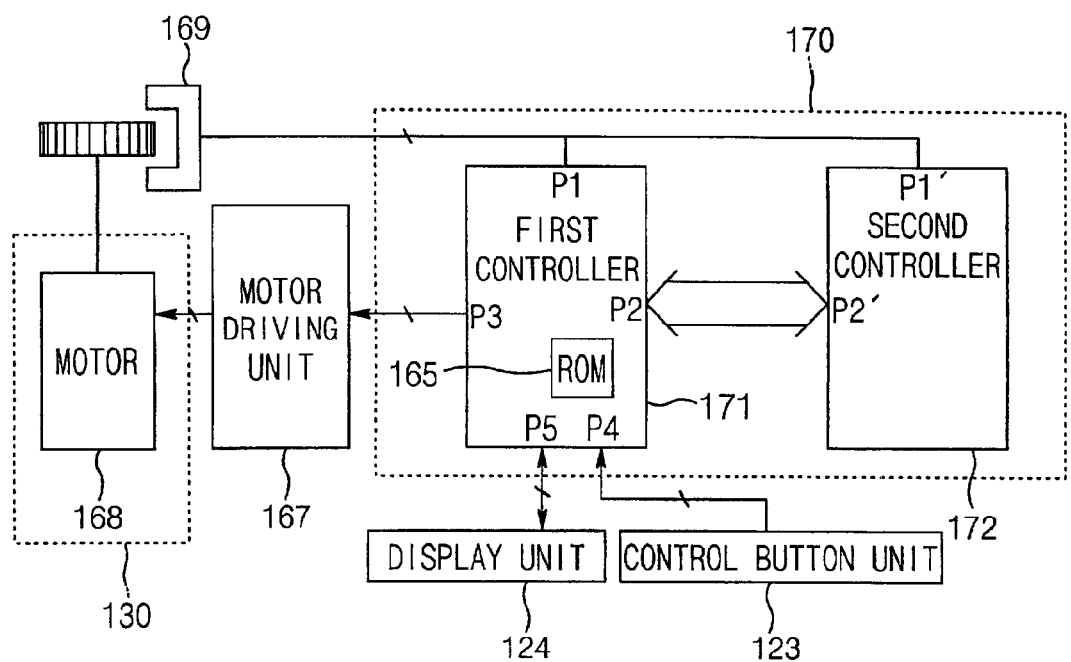
FIG. 24 is a block diagram illustrating a control circuit for the syringe device shown in FIG. 16.
Figure 25:
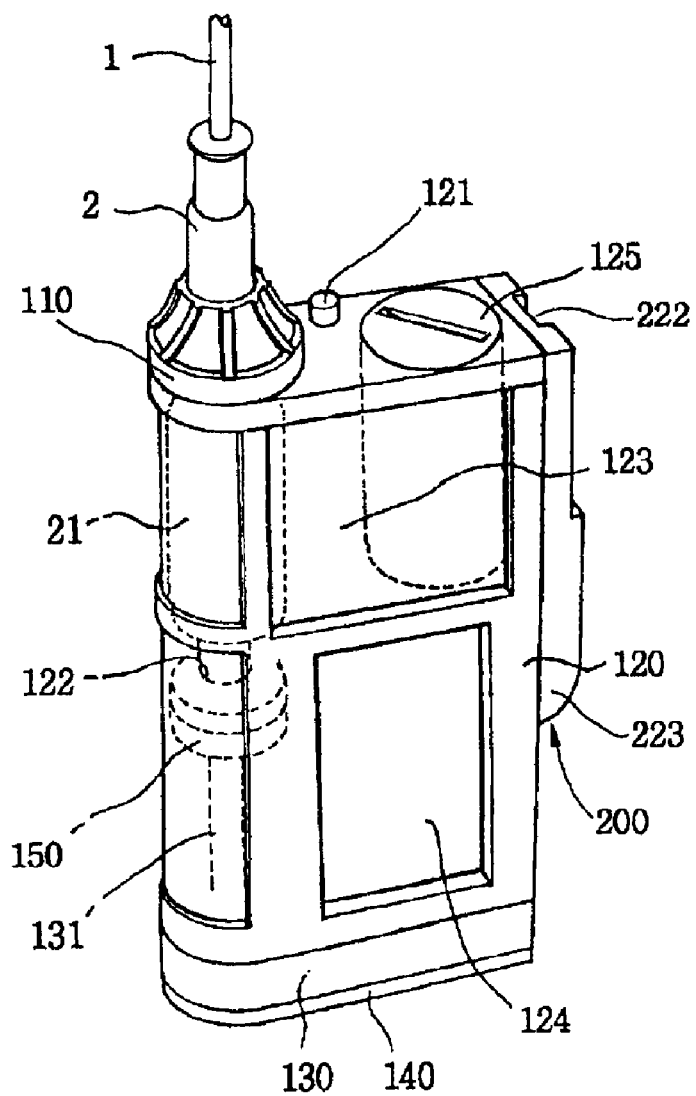
FIG. 25 is a perspective view illustrating a portable automatic insulin syringe device according to the present invention.

FIG. 25 is a perspective view illustrating a portable automatic syringe device according to the present invention. As shown in FIG. 25, the syringe device includes a housing 120, a syringe 21 separately received in the housing 120, a piston 122 slidably fitted in the syringe 21 and separately received in the housing 120, a piston pushing means 150 received in the housing 120 and adapted to vertically move the piston 122, a power transmission means 130 received in the housing 120 and adapted to generate a drive force, and a rotating shaft 131 received in the housing 120 and adapted to drive the piston pushing means 150 by the drive force transmitted from the power transmission means 130. The syringe device also includes an injection needle unit (in FIG. 25, only its feeding tube 1 and connector 2 are shown). The injection needle unit is connected to the housing 120 by means of a cover 110 which is sealably coupled to the upper end of the housing 120 at one side of the housing 120. A control button unit 123 is also installed on the housing 120. The control button unit 123 is electrically connected to a control circuit (not shown) installed in the housing 120 to control the power transmission means 130. A display 124 such as an LCD is also installed on the housing 120 in order to display the operating state of the syringe device. At the other side of the housing 120, a battery cover 125 is separately coupled to the upper end of the housing 120 in order to receive a battery in the housing 120. A reset button 121 is also installed on the housing 120 to generate a reset signal for the control circuit. A bottom cover 140 is also included in the syringe device. These configurations are similar to those of FIG. 16.

In accordance with the present invention, the syringe device further includes a blood sugar measuring unit 200 mounted to one side wall of the housing 120. The blood sugar measuring unit 200 includes a housing 223 having an insert hole 222. A measuring probe 230 is inserted into the insert hole 222, as described hereinafter.

Figure 26:
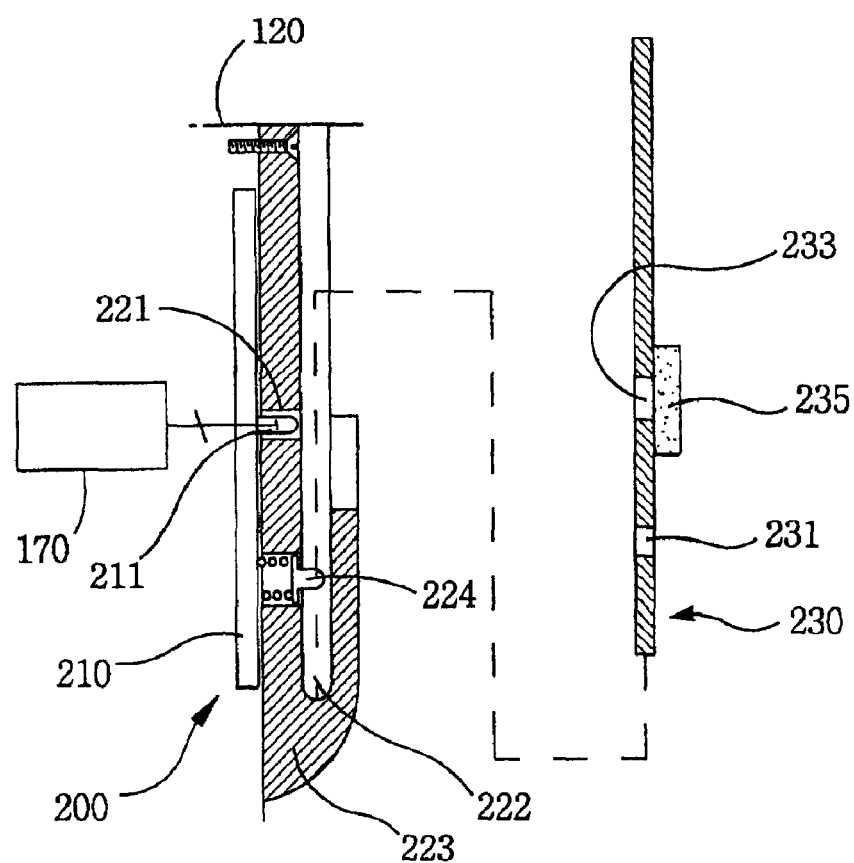
FIG. 26 is a sectional view illustrating a blood sugar measuring unit according to the present invention.
Figure 27:
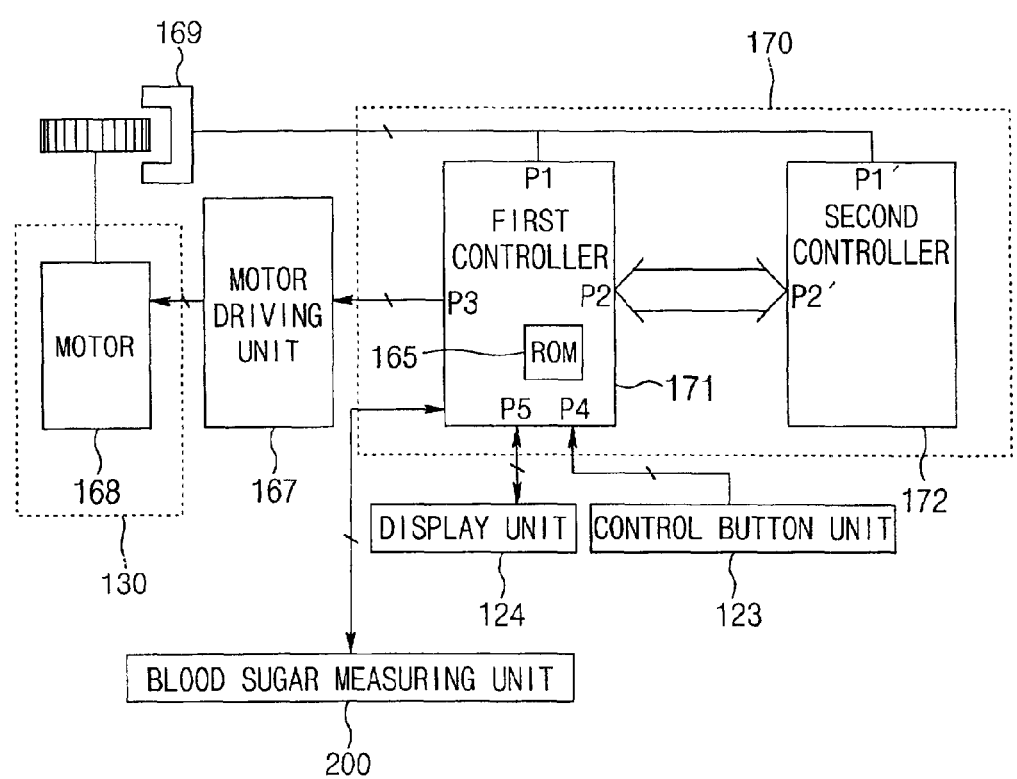
FIG. 27 is a block diagram illustrating a control circuit for the syringe device according to the present invention.

FIG. 26 is an exploded sectional view illustrating the blood sugar measuring unit 200 according to the present invention. As shown in FIG. 26, the blood sugar measuring unit 200 includes a control panel 210 adapted to control a measuring lamp 211 and to convert a measured value from the measuring lamp 211 into a signal capable of being recognized by a control unit 170 (FIG. 27). The housing 223, which is also included in the blood sugar measuring unit 200, has a lamp hole 221 for receiving the measuring lamp 211 while outwardly exposing the measuring lamp 211 therethrough. The blooding sugar measuring unit 200 also includes the measuring probe 230 which is fitted in the insert hole 222 provided at the housing 223. In order to maintain the measuring probe 230 in its fitted state, a fitting protrusion member 224 is mounted to the housing 223 in a spring-loaded state. The measuring probe 230 has a fitting hole 231 for receiving the fitting protrusion member 224, a light transmitting hole 233 formed at a position corresponding to the measuring lamp 211 in a state in which the measuring probe 230 is fitted in the insert hole 222, and a measuring plate 235 for covering the light transmitting hole 233.

FIG. 27 illustrates a control circuit for the syringe device according to the present invention. As shown in FIG. 27, the control circuit includes a control button unit 123 for generating a control signal adapted to select a desired control function, a control unit 170 provided with functions of a microcomputer and adapted to carry out a control operation in response to the control signal generated from the control button unit 123, a display unit 124 adapted to display data outputted from the control unit 170, a ROM 165 adapted to store a variety of data and programs, a motor drive unit 167 adapted to drive a motor 168 under the control of the control unit 170, and a photocoupler 169 adapted to sense a rotation of the motor 168. The rotation of the motor 168 is controlled by the motor drive unit 167. The blood sugar measuring unit 200 is electrically connected to the control unit 170 so that its operation for measuring a blood sugar level is controlled by the control unit 170. Preferably, the control unit 70 includes a pair of controllers, that is, a first controller 171 and a second controller 172, which have the same function, in order to maintain a desired function even when one of the controllers 171 and 172 is out of order. The controllers 171 and 172 have terminals P1 to P6 and terminals P1' and P2', respectively. These terminals are ports connected to data and/or bus lines, respectively. For the motor 168, a stepping motor or servo motor may be used.

Figure 28:
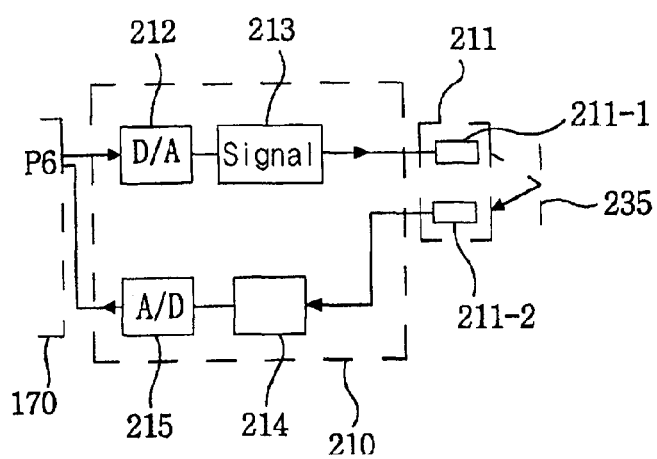
FIG. 28 is a block diagram illustrating a control panel according to the present invention.

FIG. 28 is a block diagram illustrating an embodiment of the control panel 210 according to the present invention. The control panel 210 has a configuration for receiving a command from the control unit and a measured value from the measuring lamp 211. As shown in FIG. 28, the control panel 210 includes a digital/analog (D/A) converter 212 for converting a digital signal, outputted from the control unit 170 at the terminal P6, into an analog signal, and a lamp driving unit 213 for driving a light emitting element 211-1 of the measuring lamp 211 in response to the signal from the D/A converter 212. In addition to the light emitting element 211-1, the measuring lamp 211 includes a light receiving element 211-2 adapted to receive the light from the light emitting element 211-1 reflected by the measuring plate 235. The control panel 210 also includes a signal receiving/amplifying unit 214 for receiving and amplifying an output signal from the light receiving element 211-2 of the measuring lamp 211, and an analog/digital (A/D) converter 215 for converting an output signal from the signal receiving/amplifying unit 214 into a digital signal, and applying the digital signal to the terminal P6 of the control unit 170.

Figure 29:
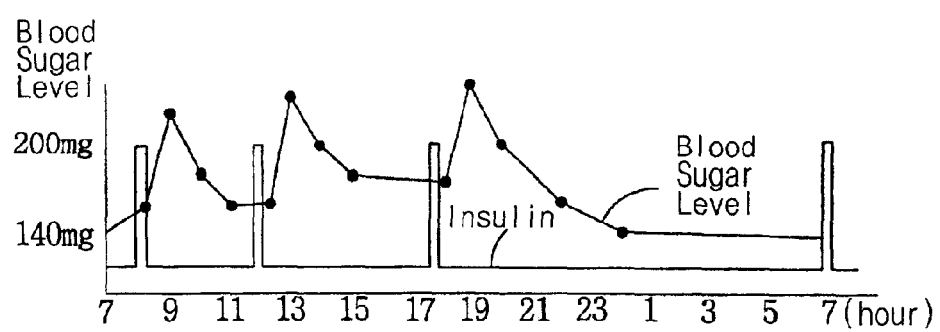
FIG. 29 is a graph of a blood sugar level and an insulin level displayed according to the present invention.

FIG. 29 is a graph displayed by the display unit according to the present invention.

Now, the operation of the portable automatic insulin syringe device having the above described configuration according to the present invention will be described. Since the insulin injection function of the syringe device is carried out in a general manner, the following description will be made mainly in conjunction with measurement of blood sugar level. The quantity of insulin dispensed to the user by the syringe device of the present invention can be displayed, as shown in FIG. 29. The measurement of blood sugar level can be easily performed using the blood sugar measuring unit 200 shown in FIG. 25. The blood sugar measuring operation of the blood sugar measuring unit 200 is controlled by the control unit 170. That is, when the control unit 170 outputs a measurement enabling signal at its terminal P6, as shown in FIG. 28, the D/A converter 212 converts the signal from the control unit 170 into an analog signal which is, in turn, amplified by the lamp driving unit 213. The amplified signal is then applied to the measuring lamp 211, so that the light emitting element 211-1 emits light. The light emitted from the light emitting element 211-1 is reflected by the measuring plate 235, and then received by the light receiving element 211-2. Thereafter, the signal received by the light receiving element 211-1 is amplified by the signal receiving/amplifying unit 214, and then converted into a corresponding digital value by the A/D converter 215. The digital value is applied to the control unit 170 at the terminal P6. The control unit 170 recognizes the value applied thereto, and outputs, to the display unit 124, the recognized value along with the time at which the value is recognized. The display unit 124 displays the recognized value, as a measured blood sugar level, in the form of a graph, as shown in FIG. 29. As seen in the graph of FIG. 29, the blood sugar level is measured every hour. The control unit 170 outputs a variation of the measured value from a reference value with the lapse of time, in the form of a graph. The type of the graph may be variously designed.

Although the preferred embodiments of the invention have been disclosed for illustrative purposes, those skilled in the art will appreciate that various modifications, additions and substitutions are possible, without departing from the scope and spirit of the invention as disclosed in the accompanying claims.

As apparent from the above description, the present invention provides a portable automatic insulin syringe device capable of measuring and displaying both the quantity of insulin dispensed to the user and the blood sugar level of the user on a display unit. Accordingly, the doctor can conveniently measure the quantity of insulin dispensed to the user and the blood sugar level of the user by simply monitoring the data displayed on the display unit, without separately measuring the insulin quantity and blood sugar level in accordance with a substitution method.

What is claimed is:

1. A portable automatic insulin syringe device adapted to enable an injection of liquid medicine for a prolonged time, comprising:
   (a) a blood sugar measuring unit mounted at one side of a pump housing and adapted to measure a blood sugar level of a user; comprising:
   (i) a housing having a lamp hole and an insert hole;
   (ii) a control panel adapted to control a measuring lamp and to convert a measured value from the measuring lamp into a signal capable of being recognized by the control unit;
   (iii) the measuring lamp received in the lamp hole while being outwardly exposed through the lamp hole;
   (iv) a measuring probe that fits into the insert hole having a measuring plate for covering the lamp hole behind the measuring probe; and
   (v) a fitting protrusion member mounted to the housing in a spring-loaded state adapted to maintain the measuring probe in a fixed position over the lamp hole,
   (b) a control unit mounted in the pump housing for controlling the blood sugar measuring unit and a syringe pump wherein a value of the blood sugar level is received by the control unit from the blood sugar measuring unit and wherein the control unit outputs a quantity of insulin and a variation of the value of the blood sugar level from a reference value with a lapse of time; and
   (c) a display unit mounted in the pump housing for simultaneously displaying the quantity of insulin dispensed to a user and a variation of the value of the blood sugar level from a reference value with the lapse of time in the form of a graph.

* * * * *